United States Patent [19]

Martin et al.

[11] Patent Number: 4,908,360
[45] Date of Patent: Mar. 13, 1990

[54] 1-AMINOALKYL-3-OXYSUBSTITUTED-4-ARYL-1,3,4,5-TETRAHYDRO-2H-1,3-BENZODIAZEPINE-2-ONES

[75] Inventors: Lawrence L. Martin, Lebanon; Joseph F. Payack, Somerset, both of N.J.

[73] Assignee: Hoechst-Roussel Pharmaceuticals Inc., Somerville, N.J.

[21] Appl. No.: 270,335

[22] Filed: Nov. 14, 1988

[51] Int. Cl.$^4$ .............. A61K 31/55; C07D 243/04
[52] U.S. Cl. .................... 514/213; 540/500
[58] Field of Search .............. 540/500; 514/213

[56] References Cited

U.S. PATENT DOCUMENTS

| | | | |
|---|---|---|---|
| 3,474,090 | 10/1969 | Wright | 540/500 |
| 4,309,424 | 1/1982 | Martin et al. | 540/567 |
| 4,374,067 | 2/1983 | Lee et al. | 540/567 |
| 4,409,145 | 10/1983 | Martin et al. | 540/567 |
| 4,459,230 | 7/1984 | Martin et al. | 540/567 |
| 4,459,231 | 7/1984 | Martin et al. | 540/567 |
| 4,461,728 | 7/1984 | Lee et al. | 540/567 |
| 4,462,933 | 7/1984 | Martin et al. | 540/567 |
| 4,469,889 | 9/1984 | Martin et al. | 540/567 |
| 4,504,680 | 3/1985 | Martin et al. | 540/567 |
| 4,709,093 | 11/1987 | Lee et al. | 540/567 |
| 4,822,914 | 4/1989 | Martin et al. | 540/567 |

FOREIGN PATENT DOCUMENTS 2566774  3/1986  France ............ 546/567

OTHER PUBLICATIONS

Geyer et al., "J. Med. Chem.", vol. 25, pp. 342–346 (1982).
Martin et al., "J. Med. Chem.", vol. 25, pp. 346–351 (1982).
Setesrak et al., "J. Med. Chem.", vol. 27, pp. 401–404.

Primary Examiner—Robert T. Bond
Attorney, Agent, or Firm—Jerome Rosenstock

[57] ABSTRACT

This invention relates to 1-aminoalkyl-3-oxysubstituted-4-aryl-1,3,4,5-tetrahydro-2H-1,3-benzodiazepine-2-ones having the formula

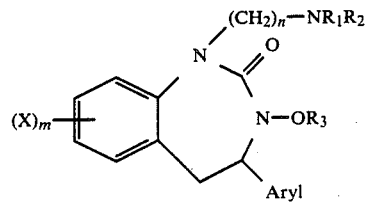

where $R_1$ and $R_2$ are each independently hydrogen, loweralkyl, aryl, arylloweralkyl, and acyl; $R_3$ is hydrogen, loweralkyl, arylloweralkyl aryl and acyl; X is hydrogen, halogen, hydroxy loweralkyl, loweralkoxy, $NO_2$, $NH_2$ and $CF_3$; m is an integer of 1 to 3, n is an integer of 1 to 3; the pharmaceutically acceptable acid addition salts thereof and where appropriate the geometric and optical isomers thereof. The compounds of this invention display utility as analgesics, calcium ion antagonists and antihypertensives.

16 Claims, No Drawings

1-AMINOALKYL-3-OXYSUBSTITUTED-4-ARYL-1,3,4,5-TETRAHYDRO-2H-1,3-BENZODIAZEPINE-2-ONES

This invention relates to compounds of the formula

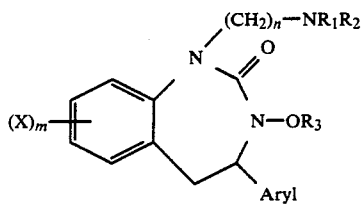 (I)

where $R_1$ and $R_2$ are each independently hydrogen, loweralkyl, aryl, arylloweralkyl, and acyl; $R_3$ is hydrogen, loweralkyl, arylloweralkyl, aryl and acyl; X is hydrogen, halogen, hydroxyloweralkyl, loweralkoxy, $NO_2$, $NH_2$ and $CF_3$; m is an integer of 1 to 3, n is an integer of 1 to 3; the pharmaceutically acceptable acid addition salts thereof and where appropriate the geometric and optical isomers thereof. The compounds of this invention display utility as calcium ion antagonists and antihypertensives.

Preferred embodiments of the invention are those substituents of Compound I where $R_1$ is selected from hydrogen and loweralkyl; $R_2$ is selected from hydrogen and loweralkyl; $R_3$ is selected from loweralkyl, acyl.

Most preferred embodiments of the invention are those of Compound I where $R_1$ is selected from hydrogen, methyl; $R_2$ is selected from hydrogen, methyl; $R_3$ is selected from methyl, acetyl.

Throughout the specification and appended claims, a given chemical formula or name shall encompass all geometric, optical and stereoisomers thereof where such isomers exist.

In the above definition, the term, "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc; the term "aryl" refers to a monovalent substituent which consists of a group, e.g. phenyl, o-tolyl, m-methoxyphenyl, etc. of the formula

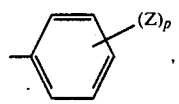

where Z and p are as defined below; the term "arylloweralkyl" refers to a monovalent substituent which consists of an aryl group, e.g. phenyl, o-tolyl, m-methoxyphenyl, etc., of the formula

where Z and p are as defined below, linked through a loweralkyl group having its free valence bond from a carbon of the loweralkyl group, and having a formula of

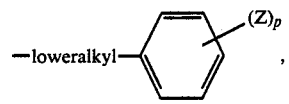

where Z is hydrogen, halogen, loweralkyl, loweralkoxy. $CF_3$, $NO_2$ and $NH_2$ and p is an integer of 1 to 4; the term "loweralkyl" in the context of

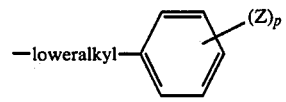

refers to a bivalent radical of the lower branched or unbranched alkyl group it is derived from, having valence bonds from the terminal carbons thereof, e.g. ethyl ($-CH_2CH_2-$), propyl ($-CH_2CH_2CH_2-$). isopropyl

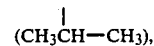

etc; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc; the term "acyl" refers to a substituent having the formula

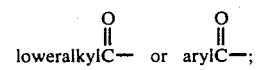

and the term "halogen" refers to a member of the halogen family consisting of fluorine, chlorine, bromine and iodine.

The compounds of the present invention are prepared in the following manner. The substituents $R_1$, $R_2$, X, $R_3$ and Z and the integers m, n and p are as defined above unless indicated otherwise.

An N-acylated-o-toluidine of the formula II is selected,

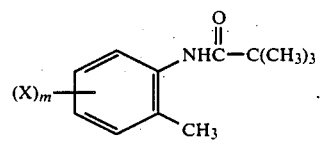 (II)

Compound II is converted to a dilithio intermediate of the formula

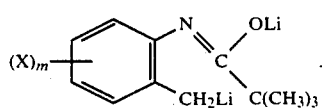 (III)

Lithiation of aromatic compounds with an n-alkyllithium compound is exemplified in J. M. Muchowski and M. Venuti, *J. Org. Chem.* 45, 4798–4801 (1980) and W. Fuhrer and H. W. Gschwend, *J. Org. Chem.* 44, 1133–1136(1979). A preferred method according to the present invention involves slowly adding a solution of n-butyllithium in a solvent therefor, such as hexane, to a solution of the N-acylated-o-toluidine (II) in an ethereal solvent such as diethyl ether, tetrahydrofuran, dimethoxyethane, and a hydrocarbon solvent, such as hexane. The ethereal solvent and hydrocarbon solvent should be substantially inert to the n-butyllithium to avoid adverse side reactions. The temperature during the addition can range from about −70° C. to about 30° C., preferably about −10° C. to about 30° C. The resulting mixture is aged from about one-half to about 5 hours, preferably about 1 to about 2 hours. The reaction is conveniently carried out at atmospheric pressure. The amount of n-butyllithium employed is up to about 10% in excess of the 2 molar equivalents required for the reactin. It is important to exclude moisture from the reaction mixture. Accordingly, the reaction is conveniently conducted in an atmosphere of a substantially dry gas, such as substantially anhydrous nitrogen.

Compound III is reacted with compound IV of the formula

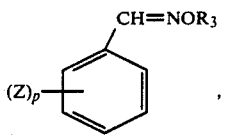

to obtain compound V of the formula

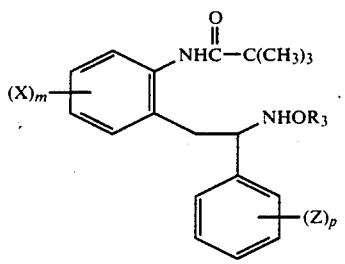

Compound IV is prepared by methods well known in the art for the synthesis of oximes and oxime ethers. Typically, the reaction of compounds III and IV are carried out in an ethereal solvent, e.g. diethylether, tetrahydrofuran, etc., at a temperature of −20° to +10° C. for 1 to 5 hours to form Compound V.

Compound V is hydrolyzed under standard hydrolyzing conditions such as for example in an aqueous solvent, e.g. water, with a mineral acid, e.g. hydrochloric, sulfuric, etc., at a temperature of 75° C. to reflux for 1 to 12 hours followed by standard basification with a base e.g. sodium hydroxide, potassium hydroxide etc., to form Compound VI

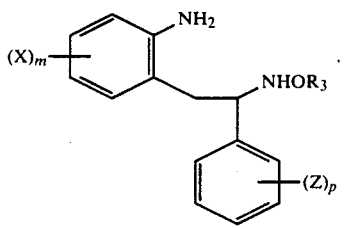

The aromatic amine VI is cyclized with a compound of the formula

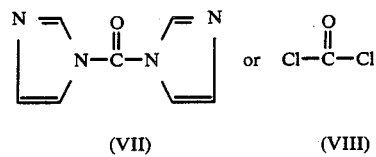

to provide Compound (IX) of the formula

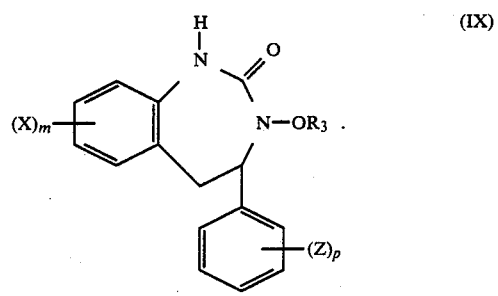

Compound VI can be cyclized with a compound of formula (VII) or formula (VIII) in a suitable solvent, such as acetonitrile, diethylether, toluene or tetrahydrofuran, or mixtures thereof. The reaction can be conducted at a temperature of from about 0° C. to the reflux temperature of the reaction mixture and at atmospheric pressure for at least about 1 hour, typically about 1 hour to about 8 hours. About 1 to about 5 molar equivalents of the compound of formula (VII) or formula (VIII) are employed.

Compound IX is then subjected to standard lithiation by reaction with n-butyllithium in an ethereal solvent, e.g. diethylether, tetrahydrofuran etc., at a temperature of −100° to 0° C. for 0.5 to 5 hours to form intermediate compound X,

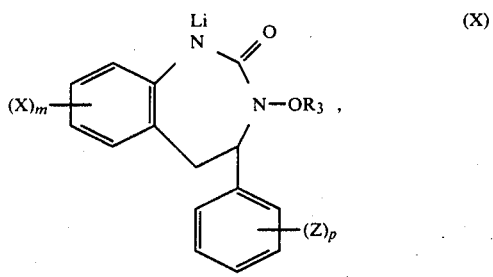

which in turn is reacted with Compound XI of the formula

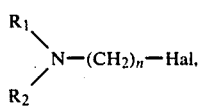

where Hal is a halogen, to form Compound I of the invention. Typically, Compounds X and XI are reacted in situ at a temperature of −78° C. to the reflux temperature of the reaction medium for 1 to 72 hours.

Compounds of the present invention are useful as analgesic agents due to their ability to alleviate pain in mammals. The activity of the compounds is demonstrated in the 2-phenyl-1,4-benzoquinone-induced writhing test in mice, a standard assay for analgesia

[Proc. Soc. Exptl. Biol. Med. 95,729 (1957)]. The analgesic activity of some of the compounds as expressed in terms of percent inhibition of writhing are given in TABLE I.

TABLE I

| Compound | Dose (subcutaneous) (mg/kg of body weight) | Inhibition in Writhing (%) |
|---|---|---|
| (±)-1-[2-(N,N—dimethylamino) ethyl]-3-methoxy-4-phenyl-1,3,4,5-tetrahydro-2H—1,3-benzodiazepine-2-one | 20 | 37 |
| (±)-1-[3-(N,N—dimethylamino) propyl]-3-methoxy-4-phenyl-1,3,4,5-tetrahydro-2H—1,3-benzodiazepine-2-one | 20 | 37 |
| dextrorphan | 15.1 | 50 |

The analgesic relief of pain is achieved when the compounds of the invention are administered to a subject requiring such treatment at an effective oral, parenteral or intravenous dose of from 0.1 to 100 mg/kg of body weight per day. A preferred effective dose within this range is from about 10 to 50 mg/kg of body weight per day. A particularly preferred effective amount is about 30 mg/kg of body weight per day. It is to be understood, however, that for any particular subject, specific dosage regimens should be adjusted according to the individual need. It is further to be understood that the dosages set forth herein are examples only and that they do not to any extent, limit the scope of practice of the invention.

The compounds of the present invention are also useful as calcium ion antagonists which are useful to control cardiovascular activities, including potential antihypertensive activity. Calcium ion antagonism is measured in the nitrendipine binding assay.

The nitrendipine binding assay is carried out in the following manner. The reagents employed are (1) 0.5 M tris Buffer, pH 7.4, prepared by combining 66.1 g of Tris HCl, 9.7 g of Tris base in 1 liter of distilled water and thereafter making a 1:10 dilution in distilled water; (2) [5-methyl-$^3$H]-Nitrendipine (70-81 Ci/mmol, obtained from New England Nuclear; and (3) Nifedipine. Tissue is prepared as follows. Male Wistar rats are killed by decapitation, hearts are removed and the ventricles are dissected away from the aorta and aortic tissue. The ventricles are rinsed and homogenized in 19 volumes of ice-cold 0.05 M Tris buffer, pH 7.4 using a Tekmar homogenizer. The homogenate is filtered through four layers of cheese cloth and centrifuged at 1,000 g for 10 minutes. The supernatant is decanted and recentrifuged at 48,000 g for 20 minutes. The resulting pellet is resuspended in the original volume of Tris buffer and recentrifuged at 48,000 g for 20 minutes. These resuspension and recentrifugation steps are repeated twice more to wash the ventricle membranes. The final pellet is resuspended in the original volume of 0.05 M Tris buffer. The assay itself employs 500 ul of ventricle membrane suspension; 50 ul of 0.5 M Tris buffer, pH 7.4; 500 $\mu$l [$^3$H]-nitrendipine; 20 $\mu$l of candidate drug; 380 $\mu$l of water in a test tube and is carried out in a darkened room. The test tubes are incubated for one hour at 25° C. The assay is stopped by rapid vacuum filtration through Whatman GF/B filters. The filters are washed three times with 5 ml of ice-cold 0.05 M Tris buffer, pH 7.4 and counted in 10 ml of Liquiscint scintillation cocktail. Specific binding is determined by the difference of total binding and binding in the presence of 0.1 $\mu$M nifedipine and is roughly 70–75% of the total binding. The total bound ligand is approximately 5% of the total added. The percent inhibition at each drug concentration is the mean of triplicate determinations. IC$_{50}$ values for the competing drug are calculated by log-probit analysis of the data.

The calcium ion antagonism activity of some of the compounds expressed as percent increase in binding are given in TABLE II.

TABLE II

| Compound | Concentration (moles) × 10$^{-5}$ | Increase in Binding (%) |
|---|---|---|
| (±)-1-[2-(N,N—dimethyl amino)ethyl]-3-methoxy-4-phenyl-1,3,4,5-tetrahydro-2H—1,3-benzodiazepine-2-one | 2.0 | 27.6 |
| (±)-1-[3-(N,N—dimethyl amino)propyl]-3-methoxy-4-phenyl-1,3,4,5-tetrahydro-2H—1,3-benzodiazepine-2-one | 2.0 | 25.7 |
| diltiazem (standard) | 1.0 | 85 |

Calcium ion antagonism, useful for example in blood pressure reduction, is achieved when the compounds of the invention are administered to a subject requiring such treatment at an effective oral, parenteral or intravenous dose of from 0.1 to 50 mg/kg of body weight per day. A preferred effective dose within this range is from about 0.1 to 10 mg/kg of body weight per day. A particularly preferred effective amount is about 3 mg/kg of body weight per day. It is to be understood, however, that for any particular subject, specific dosage regimens should be adjusted according to the individual need and the professional judgment of the person administering or supervising the administration of the compounds of the invention. It is to be further understood that the dosages set forth herein are examples only and that they do not, to any extent, limit the scope or practice of the invention.

The compounds of the present invention may be administered orally, for example, with an inert diluent or with an edible carrier. They may be enclosed in gelatin capsules or compressed into tablets. For the purpose or oral therapeutic administration, the compounds may be incorporated with excipients and used in the form of tablets, troches, capsules, elixirs, suspensions, syrups, wafers, chewing gums and the like. These preparations should contain at least 4% 1-aminoalkyl-3-oxysubstituted-4-aryl-1,3,4,5-tetrahydro-2H-1,3-benzodiazepine-2-one compounds of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0-300 milligrams of the 1-aminoalkyl-3-oxysubstituted-4-aryl-1,3,4,5-tetrahydro-2H-1, 3-benzodiazepine-2-one compounds of the present invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes, colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the 1-aminoalkyl-3-oxysubstituted-4-aryl-1,3,4,5-tetrahydro-2H-1,3-benzodiazepine-2-one derivative of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the 1-aminoalkyl-3-oxysubstituted-4-aryl-1,3,4,5-tetrahydro-2H-1,3-benzodiazepine-2-one derivative of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of some of the compounds include:
(±)-3-t-butoxy-1-[2-(N-phenyl-N-propylamino)ethyl]-4-(4-fluorophenyl)-1,3,4,5-tetrahydro-2H-1,3-benzodiazepine-2-one;
(±)-1-(2-ethylamino)ethyl-3-methoxy-4-phenyl-1,3,4,5-tetrahydro-2H-1,3-benzodiazepine-2-one;
(±)-1-[2-(N,N diethylamino)ethyl]-3-methoxy-4-phenyl-1,3,4,5-tetrahydro-2H-1,3-benzodiazepine-3-one;
(±)-1-[2-N,N-dibenzylamino)ethyl]-3-methoxy-4-phenyl-1,3,4,5-tetrahydro-2H,1,3-benzodiazepine-2-one;
(±)-1-[2-(N-pentyl-N-phenylamino)ethyl]-3-benzyloxy-4-phenyl-1,3,4,5-tetrahydro-2H-1,3-benzodiazepine-2-one;
(±)-3-acetoxy-1-[2-(N,N-dimethylamino)ethyl]-4-phenyl-1,3,4,5-tetrahydro-2H-1,3-benzodiazepine-2-one;
(±)-1-[2-(N-acetyl-N-methylamino)propyl]-3-hydroxy-4-(2-methylphenyl)-1,3,4,5-tetrahydro-2H-1,3-benzodiazepine-2-one;
(±)-1-[3-(N,N-diethylamino)propyl]-4-(2,4-dimethoxyphenyl)-1,3,4,5-tetrahydro-2H-1,3-benzodiazepine-2-one;
(±)-1-[2-(N,N-dimethylamino)ethyl]-4-(2-hydroxyphenyl)-1,3,4,5-tetrahydro-2H-1,3-benzodiazepine-2-one.

The following examples are for illustrative purposes and are not to be construed as limiting the invention disclosed herein. All temperatures are given in degrees centigrade unless indicated otherwise.

EXAMPLE 1 a.

(±)-N-[2-(2-Methoxyamino-2-phenyl)ethyl]phenyl-2,2dimethylpropanamide

A stirred, chilled (0° C.) solution of 2,2-dimethyl-N-[(2-methyl)phenyl]propanamide (84 g, 0.44 mol) and tetrahydrofuran (750 ml) was treated over 2.5 hours with a 2.5 M solution of n-butyllithium in hexane (390 ml, 0.88 mol) (nitrogen atmosphere). The solution was stirred 1 hour at −5° C. and the resulting suspension was then treated over 40 minutes with a solution of benzaldehyde-O-methyloxime (30.0 g, 0.22 mol) and tetrahydrofuran (80 ml) (temperature maintained below 10° C.). After stirring the mixture for 1 hour, methanol, (33.6 g) was added to quench the reaction. Water was added (400 ml) and the mixture was concentrated on a rotary evaporator to remove the tetrahydrofuran. The resulting aqueous phase was extracted twice with 200 ml portions of methylene chloride. The organic phase was washed once with saturated aqueous sodium chloride solution (100 ml), and was dried ($Na_2SO_4$), filtered and concentrated to yield an oil (125.8 g). A 20 g aliquot of the oil was purified by preparative high pressure liquid chromatography (HPLC) (Waters Associates Prep. LC/System 500A, silica gel, sample applied in methylene chloride, eluted with 1:2 (v/v) ethyl acetate in hexane, flow rate 200 ml/min, Gow Mac Model 80-800 UV detector) to give the purified material as an oil. A portion of the oil was triturated with ether to yield an amorphous powder of (±)-N-[2-(2-methoxyamino-2-phenyl)ethyl]phenyl-2,2-dimethylpropanamide (6.8 g, 34% based on aliquot proportions), m.p. 82°–83° C.

Analysis:
Calculated for $C_{20}H_{26}N_2O_2$: 73.59%C, 8.03%H, 8.58%N;
Found: 73.71%C, 8.09%H, 8.67%N.

b.

(±)-2-Amino-N-methoxy-α-phenylbenzeneethanamine (±)-N-[2-(2-methoxyamino-2-phenyl)ethyl]phenyl-2,2-dimethylpropanamide (9.44 g, 0.029 mol) of Example 1a was refluxed with 6N aqueous hydrochloric acid (250 ml) for 3 hours. Reaction progress was monitored by removing small aliquots of the reaction solution, basifying with 10% aqueous sodium hydroxide, extracting the basified aliquot with dichloromethane and then checking for disappearance of the starting material by thin layer chromatography (TLC) [silica gel plates, 1:1 hexane:ethyl acetate, uv detection]. The reaction was allowed to cool to room temperature, and was poured into ice (300 ml). The mixture was basified with 50% aqueous sodium hydroxide, and was extracted thrice with 200 ml portions of dichloromethane. The combined organic phase was dried with sodium sulfate, filtered, and concentrated to yield an oil (7.66 g). Purification was accomplished by preparative HPLC [Waters Associates Prep. LC/System 500; silica gel; eluted with 1:1 hexane:ethyl acetate; refractive index and uv detection; sample applied to columns in dichloromethane (15 ml)] to give 6.53 g. of an oil (93%) of (±)-2-amino-N-methoxy-α-phenylbenzeneethanamine.

Analysis:
Calculated for $C_{15}H_{18}N_2O$: 74.35%C, 7.49%H, 11,56%N;
Found: 74.30%C, 7.38%H, 11.76%N.

c.
(±)-3-Methoxy-4-phenyl-1,3,4,5-tetrahydro-2H-1,3-benzodiazepine-2-one

To a stirred solution of (±)-2-amino-N-methoxy-α-phenylbenzeneethaneamine (3.36 g, 0.0139 mole) of Example 1b and 150 ml of anhydrous ethylene glycol dimethyl ether was added a solution of 1,1′carbonyldiimidazole (2.25 g, 0.0153 mole) and 40 ml anhydrous ethylene glycol dimethyl ether at ambient temperature. The solution was refluxed for 67 hours and then concentrated to dryness. The resulting solid was purified by preparative HPLC (Waters Associates Prep LC/System 500, 2 silica gel columns, sample loaded in dichloromethane, eluted with 3:1 ethyl acetate: hexane). The appropriate fractions were combined and concentrated to afford 2.10 g (56%) of (±)-3-methoxy-4-phenyl-1,3,4,5-tetrahydro-2H-1,3-benzodiazepine-2-one,m.p.188°-190° C.

Analysis:
Calculated for $C_{16}H_{16}N_2O_2$: 71.62%C, 6.01%H, 10.44%N;
Found: 71.42%C, 6.25%H, 10.39%N.

d.
(±)-1-[2-(N,N-dimethylamino)ethyl]-3-methoxy-4-phenyl-1,3,4,5-tetrahydro-2H-1,3-benzodiazepine-2-one To a stirred, chilled (−78° C.) solution of (±)-3-methoxy-4-phenyl-1,3,4,5-tetrahydro-2H-1,3-benzodiazepine-2-one (5.0 g, 0.019 mol) of Example 1c and tetrahydrofuran (200 ml) was added n-butyllithium (9.1 ml of a 2.5 M solution in hexanes, 0.023 mol) (nitrogen atmosphere). The solution was stirred and cooled for 50 minutes, then 2-dimethylaminoethylchloride (10.22 .g, 0.095 mol) was added and the solution was allowed to warm to room temperature. The mixture was stirred and heated to 45° C. for 48 hours, with additional 2-dimethylaminoethylchloride added as follows: 16.5 hours, 14.0 g, 0.13 mol; 24 hours, 14.0 g, 0.13 mol. The mixture was then heated to reflux for 2 hours, allowed to cool, and water (400 ml) was added to quench the reaction. The tetrahydrofuran was removed in vacuo and the resulting oily aqueous phase was extracted twice with 250 ml portions of dichloromethane. The combined organic phase was washed twice with water (300 ml portions), once with saturated sodium chloride (200 ml), and was dried ($Na_2SO_4$), filtered, and concentrated to give a solid (10.45 g). The solid was purified by preparative HPLC (Waters Associates Prep LC/System 500, silica gel sample loaded in dichloromethane, eluted with 3:1 ethyl acetate:methanol). The appropriate fractions were combined, evaporated, dissolved in dichloromethane, filtered to remove all insoluble material, and concentrated to yield 1.70 g of a solid (26%). The products of several similar reactions were combined and repurified by preparative HPLC, as above, to yield 2.95 g of a solid, which was recrystallized from dichloromethane/ether to afford 2.39 g (26%) of (±)-1-[2-(N,N-dimethylamino)ethyl]-3-methoxy-4-phenyl-1,3,4,5-tetrahydro-2H-1,3-benzodiazepine-2-one,m.p.127°-128° C.

Analysis:
Calculated for $C_{20}H_{25}N_3O_2$: 70.77%C, 7.42%H, 12.38%N;
Found: 70.59%C, 7.58%H, 12.36%N.

EXAMPLE 2 a.
(±)-1-(3-Bromo)propyl-3-methoxy-4-phenyl-1,3,4,5-tetrahydro-2H-1,3-benzodiazepine-2-one To a stirred, chilled (−78° C.) solution of (±)3-methoxy-4-phenyl-1,3,4,5-tetrahydro-2H-1,3-benzodiazepine-2-one of Example 1c (5.0 g, 0.019 mol) and tetrahydrofuran (100 ml) was added n-butyllithium (9.1 ml of a 2.5 M solution in hexanes, 0.023 mol) [nitrogen atmosphere]. The solution was stirred and cooled for one hour, then 1,3-dibromopropane (30.7 g, 0.152 mol) was added and the solution was allowed to warm to room temperature. The solution was refluxed overnight (about 16 hours) and then water (80 ml) was added to quench the reaction. The tetrahydrofuran was evaporated, and the resulting oily aqueous phase was dried ($Na_2SO_4$), filtered and evaporated to yield 29.2 g of an oil. The oil was purified by preparative HPLC (Waters Associates Prep LC/System 500, 2 silica gel columns, sample loaded and eluted in 3:2 hexane:ethylacetate). The appropriate fractions were combined and evaporated to yield 6.40 g (87%) of an oil which solidified upon cooling to yield (±)-1-(3-bromo)propyl-3-methoxy-4-phenyl-1,3,4,5-tetrahydro-2H-1,3-benzodiazepine-2-one,m.p.91°-93° C.

Analysis:
Calculated for $C_{19}H_{21}N_2O_2Br$: 58.62%C, 5.44%H, 7.20%N;
Found: 59.17%C, 5.44%H, 7.21%N.

b.
(±)-1-[3-(N,N-Dimethylamino)propyl]-3-methoxy-4-phenyl-1,3,4,5-tetrahydro-2H-1,3-benzodiazepine-2-one To a stirred, chilled (−5° C.) solution of dimethylamine (3.5 g, 0.077 mol) and tetrahydrofuran (50 ml) was added over 5 minutes a solution of (±)-1-(3-bromo)propyl-3-methoxy-4-phenyl-1,3,4,5-tetrahydro-2H-1,3-benzodiazepine-2-one of Example 2a and tetrahydrofuran (50 ml). The solution was allowed to warm to room temperature, and was stirred for 3 days. Water (200 ml) was added and the tetrahydrofuran was removed in vacuo. The resulting oily aqueous phase was extracted three times with dichloromethane (200 ml portions), and the combined organic phase was dried ($Na_2SO_4$), filtered and concentrated to an oil, 2.93 g. The oil was purified by preparative HPLC (Waters Associates Prep LC/System 500, silica gel, sample loaded in dichloromethane, eluted with methanol). The appropriate fractions were combined and concentrated. The residual oil was dissolved in dichloromethane, filtered to remove insoluble material, and concentrated to an oil, which upon hexane trituration, yielded 2.03 g (75%) of (±)-1-[3-(N,N-dimethylamino)propyl]-3-methoxy-4-phenyl-1,3,4,5-tetrahydro-2H-1,3-benzodiazepine-2-one,m.p.59°-61° C.

Analysis:
Calculated for $C_{21}H_{27}N_3O_2$: 71.36%C, 7.70%H, 11.89%N;
Found: 71.24%C, 7.71%H, 11.89%N.

We claim:
1. A compound of the formula

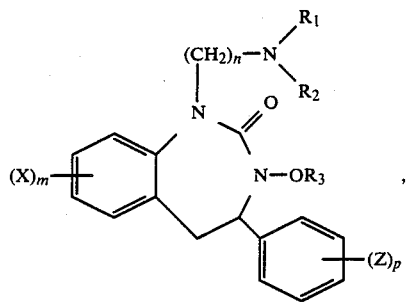

where $R_1$ and $R_2$ are each independently hydrogen, loweralkyl, aryl, of the formula

arylloweralkyl of the formula

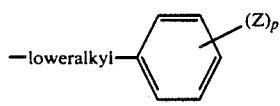

and acyl of the formula loweralkyl

or of the formula

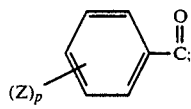

$R_3$ is hydrogen, loweralkyl, arylloweralkyl of the formula

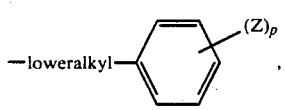

aryl of the formula

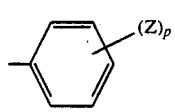

and acyl of the formula

or of the formula

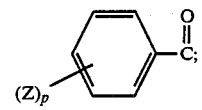

X and Z are independently hydrogen, halogen, hydroxy, loweralkyl, loweralkoxy, $NO_2$, $NH_2$ and $CF_3$, m is an integer of 1 to 3; n is an integer of 1 to 3; p is an integer of 1 to 3; and the pharmaceutically acceptable acid addition salts thereof and where applicable the individual geometric and optical isomers thereof and racemic mixtures thereof.

2. The compound as defined in claim 1 wherein $R_1$ is hydrogen, methyl; $R_2$ is hydrogen, methyl, ethyl; and $R_3$ is hydrogen, methyl, acetyl.

3. The compound as defined in claim 1 wherein $R_1$ is hydrogen, methyl; $R_2$ is methyl; and $R_3$ is methyl.

4. The compound as defined in claim 1 which is 1-[2-(N,N-dimethylamino)ethyl]-3-methoxy-4-phenyl-1,3,4,5-tetrahydro-2H-1,3benzodiazepine-2-one, and the pharmaceutically acceptable salts thereof.

5. The compound as defined in claim 1 which is 1-[3-(N,N-dimethylamino)propyl]-3-methoxy-4-phenyl-1,3,4,5-tetrahydro-2H-1,3-benzodiazepine-2-one and the pharmaceutically acceptable salts thereof.

6. An analgesic composition which comprises an effective pain alleviating amount of a compound of the formula

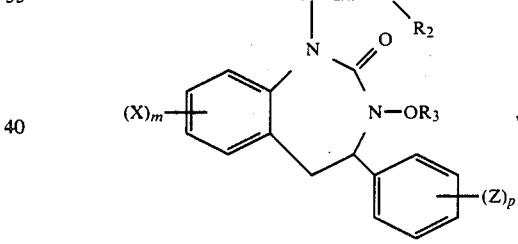

where $R_1$ and $R_2$ are each independently hydrogen, loweralkyl, aryl of the formula

arylloweralkyl of the formula

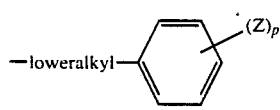

and acyl of the formula loweralkyl

or of the formula

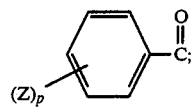

$R_3$ is hydrogen, loweralkyl, arylloweralkyl of the formula

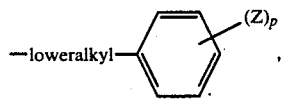

aryl of the formula

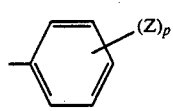

and acyl of the formula loweralkyl

or of the formula

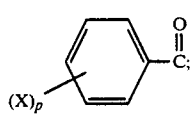

X and Z are independently hydrogen, halogen, hydroxy, loweralkyl, loweralkoxy, $NO_2$, $NH_2$ and $CF_3$; m is an integer of 1 to 3; n is an integer of 1 to 3; p is an integer of 1 to 3; and the pharmaceutically acceptable acid addition salts thereof and where applicable the individual geometric and optical isomers thereof and racemic mixtures thereof.

7. The composition as defined in claim 6 wherein $R_1$ is hydrogen, methyl; $R_2$ is hydrogen, methyl, ethyl; and $R_3$ is hydrogen, methyl, acetyl.

8. The composition as defined in claim 6 wherein $R_1$ is hydrogen, methyl; $R_2$ is methyl; and $R_3$ is methyl.

9. The composition as defined in claim 6 which is 1-[2-(N,N-dimethylamino)ethyl]-3-methoxy-4-phenyl-1,3,4,5-tetrahydro-2H-1,3-benzodiazepine-2-one, and the pharmaceutically acceptable salts thereof.

10. The composition as defined in claim 6 which is 1-[3-(N,N-dimethylamino)propyl]-3-methoxy-4-phenyl-1,3,4,5-tetrahydro-2H-1,3-benzodiazepine-2-one and the pharmaceutically acceptable salts thereof.

11. An antihypertensive composition which comprises an effective blood pressure reducing amount of a compound of the formula

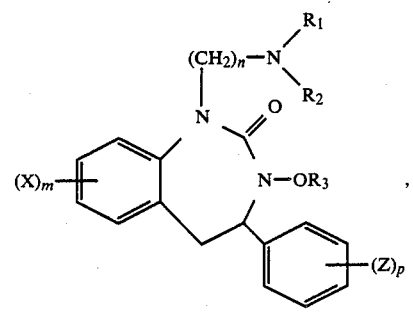

where $R_1$ and $R_2$ are each independently hydrogen, loweralkyl, aryl of the formula

arylloweralkyl of the formula

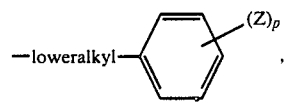

and acyl of the formula loweralkyl

or of the formula

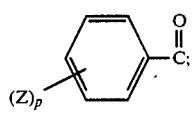

$R_3$ is hydrogen, loweralkyl, arylloweralkyl of the formula

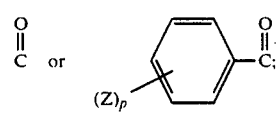

aryl of the formula

X and Z are independently hydrogen, halogen, hydroxy, loweralkyl, loweralkoxy, $NO_2$, $NH_2$ and $CF_3$, m is an integer of 1 to 3; n is an integer of 1 to 3; p is an integer of 1 to 3; and the pharmaceutically acceptable acid addition salts thereof and where applicable the individual geometric and optical isomers thereof and racemic mixtures thereof.

12. The composition as defined in claim 11 wherein $R_1$ is hydrogen, methyl; $R_2$ is hydrogen, methyl, ethyl; and $R_3$ is hydrogen, methyl, acetyl.

13. The composition as defined in claim 11 which is 1-[2-(N,N-dimethylamino)ethyl]-3-methoxy-4-phenyl-1,3,4,5-tetrahydro-2H-1,3-benzodiazepine-2-one, and the pharmaceutically acceptable salts thereof.

14. The composition as defined in claim 11 which is 1-[3-(N,N-dimethylamino)-propyl]-3-methoxy-4-phenyl-1,3,4,5-tetrahydro-2H-1,3-benzodiazepine-2-one and the pharmaceutically acceptable salts thereof.

15. A method of alleviating pain in a mammal which comprises administering to a mammal a pain alleviating effective amount of a compound of the formula

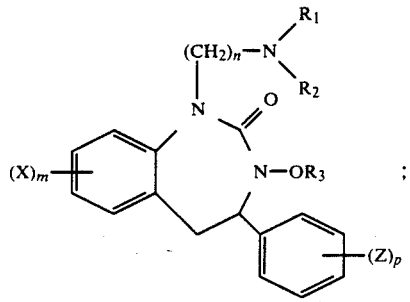

where $R_1$ and $R_2$ are each independently hydrogen, loweralkyl, aryl of the

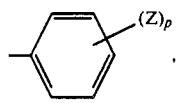

arylloweralkyl of the formula

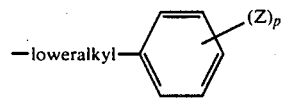

and acyl of the formula loweralkyl

or of the formula

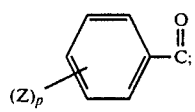

$R_3$ is hydrogen, loweralkyl, arylloweralkyl of the formula

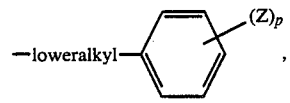

aryl of the formula

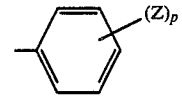

and acyl of the formula loweralkyl

or of the formula

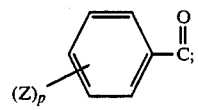

X and Z are independently hydrogen, halogen, hydroxy, loweralkyl, loweralkoxy, $NO_2$, $NH_2$ and $CF_3$, m is an integer of 1 to 3; n is an integer of 1 to 3; p is an integer of 1 to 3; and the pharmaceutically acceptable acid addition salts thereof and where applicable the individual geometric and optical isomers thereof and racemic mixtures thereof.

16. A method of reducing blood pressure in a mammal which comprises administering to a mammal an effective blood pressure reducing amount of a compound of the formula

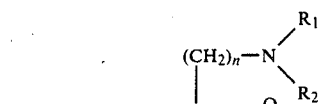

where $R_1$ and $R_2$ are each independently hydrogen, loweralkyl, aryl of the formula

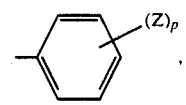

arylloweralkyl of the formula

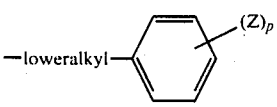

and acyl of the formula loweralkyl 

or of the formula

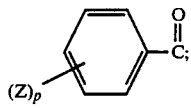

$R_3$ is hydrogen, loweralkyl, arylloweralkyl of the formula

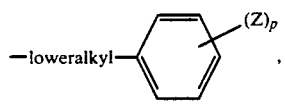

aryl of the formula

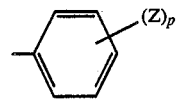

and acyl of the formula loweralkyl

or of the formula

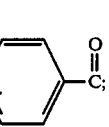

X and Z are independently hydrogen, halogen, hydroxy, loweralkyl, loweralkoxy, $NO_2$, $NH_2$ and $CF_3$, m is an integer of 1 to 3; n is an integer of 1 to 3; p is an integer of 1 to 3; and the pharmaceutically acceptable acid addition salts thereof and where applicable the individual geometric and optical isomers thereof and racemic mixtures thereof.

* * * * *